United States Patent [19]

Straihammer et al.

[11] 4,278,428
[45] Jul. 14, 1981

[54] DENTAL HANDPIECE

[75] Inventors: Reinhard Straihammer, Einhausen; Hans J. Klose, Hamsbach; Werner Schuss, Heppenheim, all of Fed. Rep. of Germany

[73] Assignee: Siemens Aktiengesellschaft, Berlin & Munich, Fed. Rep. of Germany

[21] Appl. No.: 100,000

[22] Filed: Dec. 4, 1979

[30] Foreign Application Priority Data

Dec. 22, 1978 [DE] Fed. Rep. of Germany ....... 2855797

[51] Int. Cl.$^3$ .............................................. A61C 1/08
[52] U.S. Cl. ..................................... 433/105; 433/126
[58] Field of Search ............... 433/105, 130, 126, 133, 433/146; 408/133; 74/416, 417, 332, 812

[56] References Cited

U.S. PATENT DOCUMENTS

| 1,490,796 | 4/1924 | Blomberg | 74/812 |
| 3,092,908 | 6/1963 | Flatland | 433/92 |
| 3,229,369 | 1/1966 | Hoffmeister et al. | 433/105 |
| 3,436,980 | 4/1969 | Loge et al. | 433/105 |
| 3,665,606 | 5/1972 | Saupe | 433/126 |
| 3,815,240 | 6/1974 | Loge | 433/126 |
| 3,942,392 | 3/1976 | Page, Jr. et al. | 433/105 |
| 4,047,301 | 9/1977 | Eibofner | 433/130 |

FOREIGN PATENT DOCUMENTS

| 283565 | 4/1915 | Fed. Rep. of Germany | 433/130 |
| 890118 | 9/1953 | Fed. Rep. of Germany | 433/130 |
| 1279892 | 10/1968 | Fed. Rep. of Germany | 433/105 |
| 2810044 | 9/1979 | Fed. Rep. of Germany | 433/126 |
| 1324852 | 12/1963 | France | 433/126 |
| 751618 | 7/1956 | United Kingdom | 433/105 |

Primary Examiner—Gene Mancene
Assistant Examiner—John J. Wilson
Attorney, Agent, or Firm—Hill, Van Santen, Steadman, Chiara & Simpson

[57] ABSTRACT

A dental handpiece with at least two drive shaft sections for transmitting the rotary motion from a drive motor to an acceptance socket which is rotatably mounted in a head part of the handpiece, each of the drive shaft sections being arranged with their axes at an angle to one another and one of the two drive shaft sections having two coaxial gears which have different numbers of teeth and the other drive shaft section having at least one gear characterized by one of the two sections being mounted for axial displacement between two positions with one of the positions having one of the two gears in engagement with a gear and the other position having the other of the two gears in engagement with a gear. The gears on the drive shaft sections can be selected so that in one of the positions a direct drive can be obtained and in the other position either a step-up or step-down ratio can be obtained. In one embodiment, a single gear of the one section coacts with the two gears of the other section. In another embodiment, each of the drive shafts have two gears with the axial displacement between the two gears such that one pair of gears is in engagement when the displaceable shaft is in one position and a second pair of gears is in engagement when the section is in the second position.

26 Claims, 12 Drawing Figures

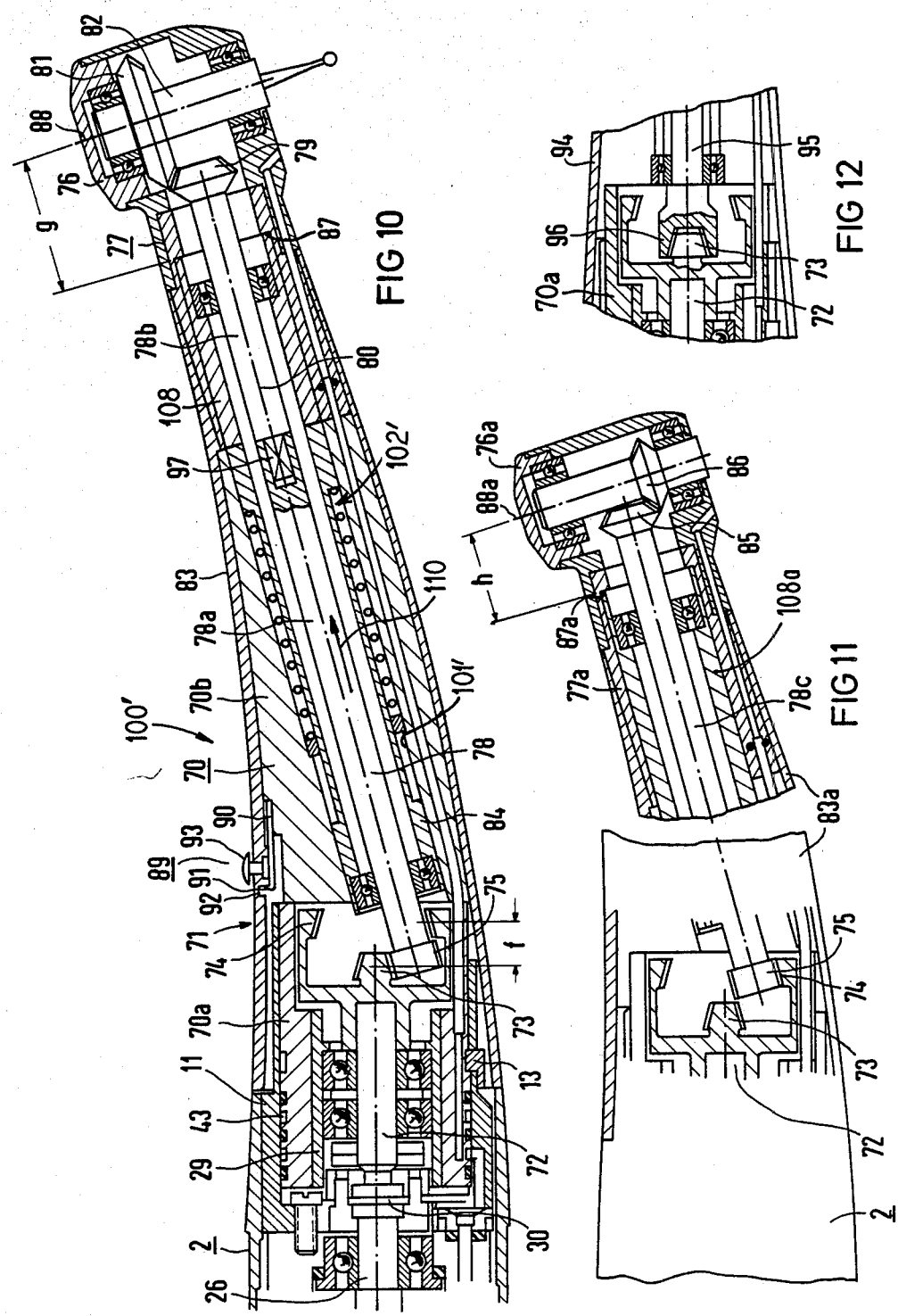

DENTAL HANDPIECE

BACKGROUND OF THE INVENTION

The present invention relates to a dental handpiece which has at least two drive shaft sections, which are arranged with their axes forming an angle with one another and form part of a drive train for transmission of the rotary motion from a drive motor of the handpiece to an acceptance socket which receives a tool and is rotatably mounted in a head part of the handpiece. To transfer motion between the drive section, the drive sections are provided with gears and at least one of the drive sections is provided with two coaxial gears having different numbers of teeth so that by axially shifting one of the sections relative to the other section, different gear combinations are in meshing engagement to produce different drive ratios between the two sections.

In a known dental handpiece such as disclosed in German A.S. No. 1,219,170, the drive train means, which transfers rotation from the drive motor to the acceptance socket in the head part, is subdivided into two drive shaft sections with one of the drive shaft sections being in a handpiece part directly connected to the motor and the other drive shaft section being in a portion of the head part. One of the two drive shaft sections is provided with a single gear and the other is provided with a pair of coaxial gears arranged with their teeth lying essentially in one plane and having different numbers of teeth. By connecting the head part and the handpiece part together in different positions so that the shaft section having the single gear is in one of two axial positions, the single gear can be in meshing engagement with either the smaller or the larger gear on the other drive shaft section. By selecting the gears, it is possible to have a direct drive with a 1:1 ratio or either a step-up in the RPM's of 1:3 RPM ratio or a step-down with a 3:1 RPM ratio. To obtain this step-down ratio the pair of gears are connected to the end of the shaft section, which is supported in the head part and to obtain the step-up in the ratio, the pair of gears are provided on the shaft section supported in the handpiece part. While this dental handpiece enables providing two different drive ratios, in order to obtain both a step-up and step-down of the ratios, various drive motors and/or handpiece and head parts for connection to the drive motors, which parts have been appropriately designed, must be provided. Since a Dentist will work with both a step-down as well as step-up drive RPM's, he must have a plurality of drive motors, or respectively, handpiece parts of the drive side according to this known handpiece structure.

A further disadvantage of the above mentioned dental handpiece is that the gear arrangement or transmission, which provides the two step ratio, greatly increases the exterior diameter of the handpiece particularly in the area of the bend of the angle piece. Furthermore, because the change in the RPM is obtained by connecting the handpiece portion and the head part together in different positions relative to the axis, the handpiece cannot have a portion that is free to rotate or twist relative to the drive motor. Moreover, the angle at the angle piece for this design is approximately 20° to the longitudinal axis of the drive motor and such an angle, which is necessary for this structure is to abrupt and thus reduces the ease in the manipulation of the handpiece. Due to the large overall diameter, the abrupt angle at the angle piece and the lack of a rotatable connection, manipulation of this handpiece structure leaves something to be desired.

SUMMARY OF THE INVENTION

The present invention is directed to providing a handpiece structure, which is improved and simplified in comparison to the known structure. In particular, the handpiece structure of the present invention has the goal of providing a device, which can obtain a direct drive transmission and both a step-down as well as a step-up transmission of the drive RPM with a single drive part. In addition, there is a structure which enables the reduction of the exterior diameter particularly in the area of the transmission change and to create a softer angular transition in the area of the angle of the angle piece.

To accomplish these tasks, the invention is directed to an improvement in the dental handpiece having a drive motor, an acceptance socket for a tool being mounted for rotation in the head part of the handpiece and a drive means for transmitting the rotary motion of the drive motor to the acceptance socket, said drive train means including at least two drive shaft sections with the axis of the pair of said sections being arranged to an angle to one another, the first drive shaft section of the pair having a first and second coaxial drive gear with each gear having a different number of teeth, the second drive shaft section of said pair having at least one gear, means for selectively forming a first coupling and a second coupling between the first and second shaft drive sections, said first coupling having a first gear of the first shaft section being in engagement with a gear on the second shaft section and the second gear being out of engagement and the second coupling being formed by a second gear of the first shaft section being in engagement with a gear on the second shaft section and the first gear being out of engagement, and said first coupling having a different drive ratio between the first and the second shaft than a drive ratio for the second coupling. The improvement comprises said means for selectively forming the first and second couplings including means for mounting one of said first and second shaft sections for axial movement between a first position forming the first coupling and a second position forming the second coupling and means for axially displacing said one shaft section between said first and second position.

In one embodiment of the invention, the first and second shaft sections are disposed in a handpiece part and a third drive shaft section is arranged in the head part. The second shaft section of this embodiment is provided at each end with a first and second axially displaced gears and the first and second gear on the first section are also axially displaced by an amount greater than the amount between the gears of the second section. The means for displacing the second section is a portion of the head part so that a selection of one head part enables a step-down in ratio, the selection of a second head part enables a step-up in the ratio and a selection of a third part enables provision of a direct drive with a 1:1 ratio.

In another embodiment, the second shaft section is supplied with only a single gear, which meshes with both of the first and second gears of the first shaft section and again the head part has a sleeve or portion which causes displacement of the second shaft section so that by changing the head part, two different ratios can be obtained.

The changing gearing in accordance with the present invention enables achieving a step-down as well as a step-up of the RPM and if desired, a direct transmission in the ratio 1:1 with a single handpiece part without having to interchange the majority of the handpiece parts which was necessary in the prior known devices. By placing the area of the gear in engagement of the drive shaft sections on the drive side with a displaceable drive shaft section relatively close to the drive motor part, the handpiece can be designed to have a very thin cross section which is an important advantage. In the present invention, when a change of the gear ratio such as a step-down or a step-up is desired, only the head part need be interchanged and the central drive gears and section supplied in the handpiece part remain connected to the drive motor part.

Another advantage of the present invention is that the gradual transition in the angle at the angle piece can occur in two stages or steps so that the center line of the drive shaft section directly coupled to the drive motor and the drive shaft section directly coupled to the head part form an angle of approximately 10° with the intermediate or middle drive shaft section. Thus, a particularly soft transition from the straight drive motor part to the head part is achieved and the parts still have space present for conducting cooling lines to a nozzle adjacent the acceptance socket of the head part.

BRIEF DESCRIPTION OF THE DRAWINGS

FIG. 10 is a longitudinal cross sectional view of an embodiment of a handpiece in accordance with the present invention;

FIG. 11 is a partial cross sectional view of the embodiment of FIG. 10 with a different headpiece; and FIG. 12 is a partial longitudinal view of the embodiment of FIG. 10 with a straight handpiece attached thereto.

DESCRIPTION OF THE PREFERRED EMBODIMENTS

Figure 1:
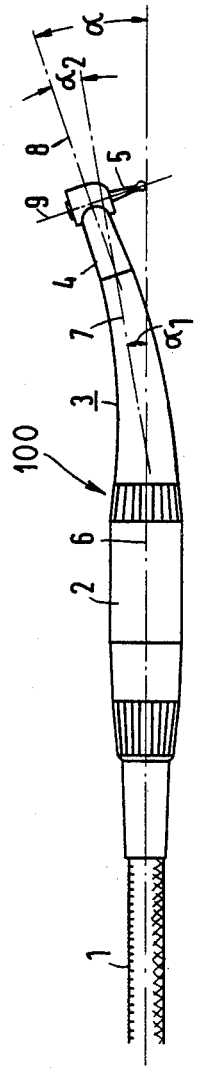
FIG. 1 is a side elevational view of a dental handpiece in accordance with the present invention having a drive motor part, an angled handpiece part and a head part.

The principles of the present invention are particularly useful in a dental handpiece generally indicated at 100 in FIG. 1. The dental handpiece 100 is composed of a drive motor section or part 2, which is connected to a supply hose 1, which extends to a source for electrical current for the motor and sources of cooling fluid whose use will be discussed hereinafter. A handpiece part or grip section 3 is connected to the drive motor portion or part 2 and extends to a head part 4 which has a housing rotatably supporting a tool 5. For transmitting the rotary motion from the drive motor in the drive motor part 2 to the tool 5, the handpiece contains a drive train means including a plurality of drive shaft sections which are engaged with one another and whose axes are provided with the reference symbols 6, 7, 8 and 9.

The angle of inclination $\alpha$, which is the angle between the axis 8 for the head part 4 and the axis 6 for the drive motor part 2, for a number of reasons according to operating technology generally lies between 18° to 21° and is the angle of the angel piece or portion of the grip section 3. As illustrated, the angle of inclination $\alpha$ is formed in stages by angle $\alpha_1$ and $\alpha_2$, wherein $\alpha_1$ is determined by the point of intersection of the two axes 6 and 7 and $\alpha_2$ is determined by the point of intersection of the axes 8 and 7. The two angles $\alpha_1$ and $\alpha_2$ are dimensioned in such a manner that upon consideration of the necessary gear step-up or step-down of the module or respectively, the number of teeth of the gears required for reasons of stability, a harmonic, external contour with a continuously decreasing exterior diameter from the one end to the other end of the handpiece can be achieved without increasing the length of the handpiece. It is expedient if both angles $\alpha_1$ and $\alpha_2$ are greater than one-fourth the total angle $\alpha$. Preferably, the angles of $\alpha_1$ and $\alpha_2$ are approximately half of the total angle $\alpha$ and have a range of approximately 8° to 12°.

Figure 2:
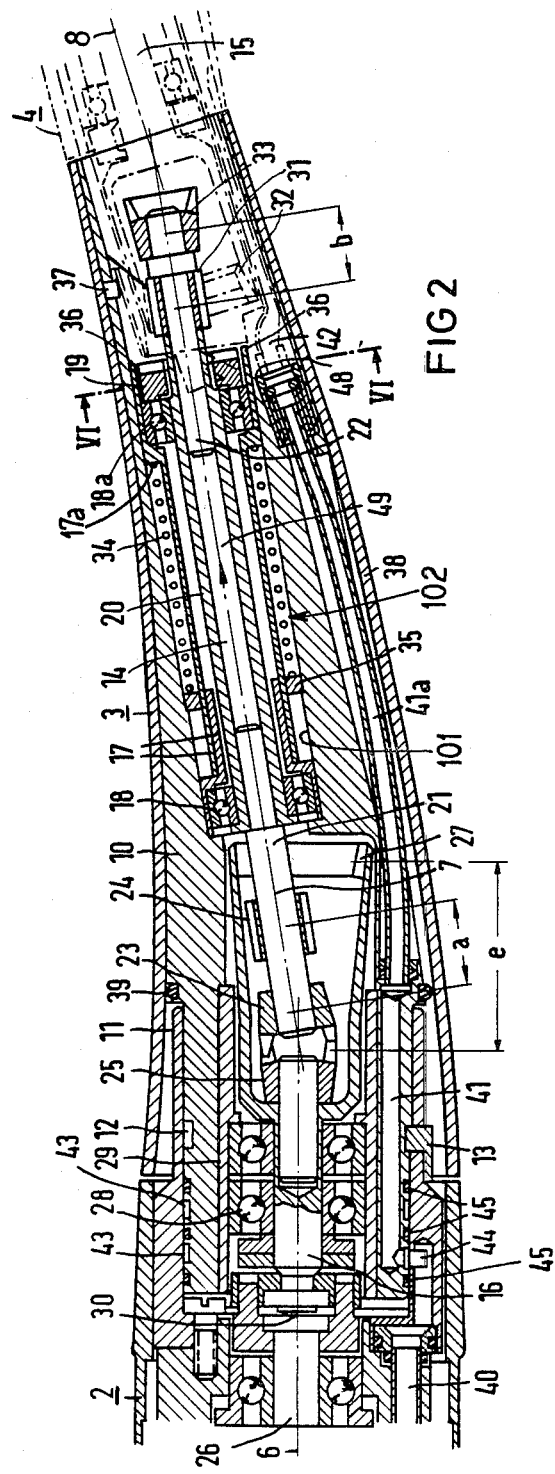
FIG. 2 is a longitudinal cross sectional view of a portion of the dental handpiece of FIG. 1.

In FIG. 2, the handpiece part or grip section 3 along with part of the motor drive part 2 are illustrated and the head part 4 is shown in chain lines. The handpiece part 3 contains a basic body member or portion 10. As illustrated, the part or portion 10 is connected to the motor part 2 by being telescopically received in a guide bushing or sleeve 11 of the part 2 so that the grip section 3 and member 10 have a rotatable connection with the drive motor part 2. The guide bushing or sleeve 11 extends concentric to the drive shaft axis 6 of which the drive shaft 26 of the motor lies and which axis 6 is the axis of symmetry for the motor part 2. As illustrated, the member 10 is rotatably received in the guide sleeve 11 but is held from axial displacement by a stop bolt 13 of the known construction which is received in the annular groove 12 of the member 10.

The member 10 supports a first drive shaft section 16 for rotation on an axis 6 and supports a second drive shaft section 14 to rotate on an axis 7. The head part 4 supports a third drive shaft sections 15 to rotate on the axis 8. The drive shaft section 14 is formed by a tubular member 20, which receives solid shaft portions 21 and 22 at each end. To mount the shaft portion 14 in a bore 101 in the member 10, mounting means, which are generally indicated at 102, include a hollow sleeve member 17 which is formed by a pair of sleeves that are secured together. The sleeve member 17 supports races of ball bearings 18 and 18a which bearings rotatably support the tubular sleeve 20 of the second shaft section 14. As illustrated, the right hand end of the sleeve member 17, which terminates in an end surface 36, receives a slotted ring 19 to secure one of the bearings 18a therein.

The shaft 21, which is pressed into the end of the tubular member 20, supports a first gear 23 and a second gear 24 with the first gear 23 being a crown gear disposed at the end and axially displaced a distance a from the second gear 24 which is a spur gear. As illustrated in FIG. 2, the crown gear 23 is engaged with a crown gear 25 of the first shaft section 16 and both crown gears 23 and 25 have the same number of teeth so that the RPM's of the shaft 26 of the drive motor 2 are directly transmitted to the drive shaft section 14 via the drive shaft section 16 and therefore a ratio of 1:1 is provided. At an interval e the drive shaft section 16 also has a coaxial second gear 27, whose teeth are on an inside surface of a cup-shaped member, which receives the gear 25, and extend towards the axis of the drive shaft. The teeth of the gear 27 will engage with the spur gear 24 when the drive shaft section 14 has been displaced in the direction of arrow 49 by an amount to enable engagement of the second gear 24 of the section 14 with the second gear 27 and disengagement of the crown gears 23 and 25 which are the first gears of each of the shaft sections.

As illustrated, the first drive shaft section 16 is releasably coupled by a coupling device 30 to the drive shaft 26 of the drive motor. The shaft 16 is supported for rotation by bearings 28 in a sleeve or bushing 29 which is received in a bore in the member 10.

At the other end of the shaft 14, the shaft 22 is provided with two axially spaced gears including a spur gear 31 and a crown gear 33. As illustrated, the spur gear 31 will engage with a gear 32 on the shaft section 15, which gear 32 (best illustrated in FIG. 3) has a structure similar to the gear 27 on the shaft section 16. The gear 33 is illustrated as a crown and is pressed on the pen-like shaft 22 at an axial distance b from the gear 31. In the position illustrated, the crown gear 33 is disengaged from any gear part of the drive shaft section 15.

The means for mounting enables axial displacement of one of the shaft sections such as the second shaft section 14 from a first position with the crown gears 23 and 25 in engagement to a second position with the spur gear 24 in engagement with the gear 27. The means 102 accomplishes this by the sleeve member 17 being slideably received in the bore 101 and having a biasing means such as the spring 34 acting between a ring shaped stop 35 and shoulder 17a to urge displacement of the sleeve 17 and the shaft 14 in the direction of arrow 49. When the head part 4 is removed, the entire device will be displaced in the direction 49 until the end surface 36 of the sleeve member 17 engages a stop detent 37.

A sleeve member or shell 38, which may be secured to the head part 4, is telescopically received on the basic body or member 10 and engages an O ring 39, which is supported on an exterior surface of the part 10. The sleeve 38 together with the head part 4 is releasably connected with the basic body member 10 by snap-in means, which are located adjacent an end surface 48 of the member 10 which surface 48 is adjacent to the head part 4 and this snap-in means is discussed in greater detail hereinafter. It should be noted, that the axial positioning of the head part 4 in the member 10 and thus the axial position of the drive shaft section 14 which is required for engagement of certain gear pairs is determined by the axial length of the head part which is inserted into the member 10.

As mentioned hereinbefore, the supply line 1 includes cooling lines extending to a source. These cooling lines are connected to cooling lines such as 40 in the motor part 2, the cooling lines such as 40 in the motor part 2 is connected to a cooling 41, which has an extension 41a that is connected to a cooling line 42 in the head part 4. These cooling lines enable conducting a media, such as air and water, up to a cooling spray nozzle adjacent the tool 5. To form a transfer of the media from the cooling line 40 to the cooling 41, annular channels 43 are formed on an outer surface of the member 10 and are in communication with a radial channel 44 in the bushing 11. To seal each of the channels 43, O ring seals 45 are provided so that the member 10 can be rotated relative to the bushing 11 and still convey fluid. It should be noted that in FIG. 2 only one cooling channel arrangement is illustrated although two grooves 43 are provided to enable separately conveying two fluids to the nozzle in the part.

Figure 3:
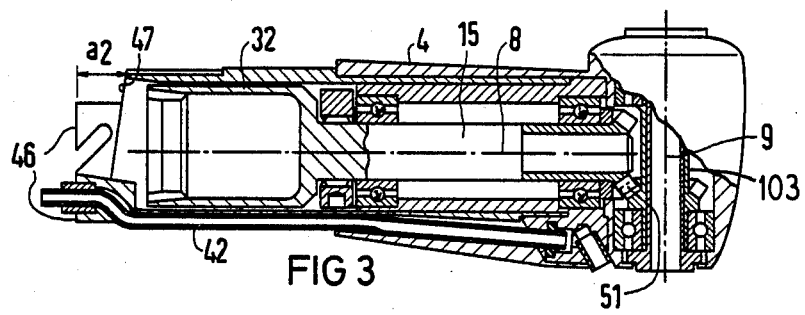
FIG. 3 is a longitudinal cross sectional view of an angled head part utilized in the handpiece of the present invention.

The head part 4, which is illustrated in FIG. 3, has a sleeve portion surrounding the gear 32, which is illustrated as being provided on the shaft section 15. The sleeve portion surrounding the shaft section is provided with two end faces or surfaces 46 and 47 which are axially displaced a distance $a_2$. When the part 4 is connected to the grip section 3, the surface 47 will engage the end face 36 of the means for mounting 102 and the end face 46 rests against the end face 48 of the body 10. The portion having an end face 46 also has portions forming part of the snap-on means for interconnecting the head part 4 on the grip section. The shaft section 15 at end opposite the gear 32 has a bevel gear which is engaged with a bevel gear on a tubular socket 103 to form an engaged gear pair 51. The tubular socket 103 extends on an axis 9 which is at right angles to the axis 8 of the shaft section 15. It should be noted, that the head part 4 has appropriate bearings for rotatably supporting both the socket 103 and the head shaft section 15. In addition, the cooling medium lines 42 terminates in a nozzle for directing the cooling medium at the tool in the socket 103.

Figure 4:
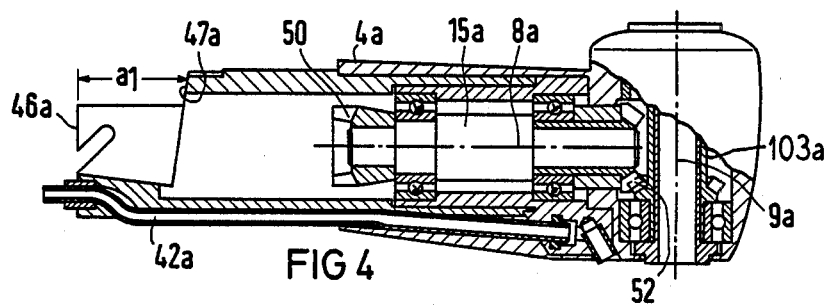
FIG. 4 is a longitudinal cross sectional view of another embodiment of the angled head part utilized in the handpiece of the present invention.

A second head portion 4a is illustrated in FIG. 4 and rotatably supports a third shaft section 15a. The shaft section 15a on the one end has a gear such a crown gear 50 and on the other end is provided with a bevel gear of a bevel gear pair 52 that transfers rotation to the socket 103a which extends on an axis 9a which is perpendicular to the axis 8a of the shaft 15a. The sleeve of the device surrounding the shaft 15a has surfaces 46a and 47a which are spaced apart by a distance $a_1$. Thus, when the part 4a is inserted and connected to the member 10 the surface 47a is axially displaced from the position of the surface 47 so that the spring 34 can shift the shaft 14 to a second position with the crown gear 33 engaging the crown gear 50. The amount of shifting is the difference between the distances or intervals $a_1$ and $a_2$.

With the head part 4 received on the handpiece part 3, the sleeve portion terminating at the surface 47 acts to shift the means for mounting 102 to a first position with the crown gear 23 engaged to the crown gear 25 and the gear 31 engaged with the gear 32 of the shaft 15. Since the crown 23 and 25 have substantially the same number of teeth, the drive ratio therebetween at that connection is a 1:1 ratio. However, because the number of teeth on the gear 32 is 2½ times the number of teeth on the gear 31, the step-down ratio at that connection is 2.5:1. Thus the RPM's applied to the shaft 15 are again step-down at the bevel gear pair 51 by a ratio of approximately 1.2:1 so that a total step-down would be approximately 3:1.

By removing the part 4 and applying the head part 4a, the sleeve of the part 4a allows the shaft section 14 to shift to the second position with the crown gears 23 and 25 out of engagement but the spur gear 24 in engagement with the gear 27. In addition, the crown gear 33 is engaged with the crown gear 50 of the head part 4a. Because the gear 27 has substantially 2.5 times the number of teeth as the gear 24, a step-up ratio occurs at the engagement of the gear 24 with the gear 27 of 1:2.5. The crown gears 33 and 50 are also in engagement but because they have the same number of teeth, they have a direct transmission of the RPM with the ratio 1:1. An additional step-up in the ratio applied to the socket 103a is accomplished by the bevel gear pair 52 which has a ratio of 1:1.2 and thus a total step-up in the RPM of approximately 1:3 is obtained.

The head part 4 and 4a are substantially the same except for the distance between the surface measured by the distance $a_1$ and $a_2$. Thus, this distance $a_1$ and $a_2$ determines how far the surface 47 or 47a will be inserted into the member 10 and therefore determine whether or not the displaceable shaft 14 is in the first or second position.

If the handpiece is to use a straight tool guidance and is to have a direct transmission with no step-up or step-down, then a head part 4b (best illustrated in FIG. 5) is utilized. In the head part 4b, a shaft section 15b terminates in an acceptance socket 103b for the tool and lies on the axis 8b. One end of the shaft 15b supports a gear such as a crown gear 53. The surfaces 47b and 46b are spaced apart a distance $a_2$ which is the same as the distance between the surfaces 46 and 47 of the head part 4. Thus, when the head part 4b is put in place, the axis 8b lies parallel but displaced to the axis 8 in FIG. 2 and the shaft section 14 is displaced to the first position with the gears 23 and 25 being engaged and the gear 33 is engaged to the gear 53 to provide a direct transmission with a 1:1 ratio. It should be noted that because of the different gear pairing or engagement, the distances of the gears from the surfaces 46, 46a and 46b are different. It also should be noted that if an angled head part such as the head part 4 is to have a 1:1 ratio, this head part will have the distance $a_2$ and have a crown gear at the same distance from the surface 47 as the crown gear 53.

Figure 6:
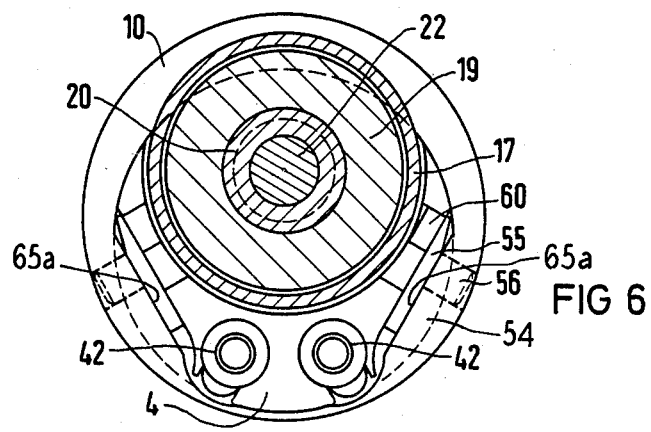
FIG. 6 is a cross sectional view taken along the lines VI—VI of FIG. 2.
Figure 7:
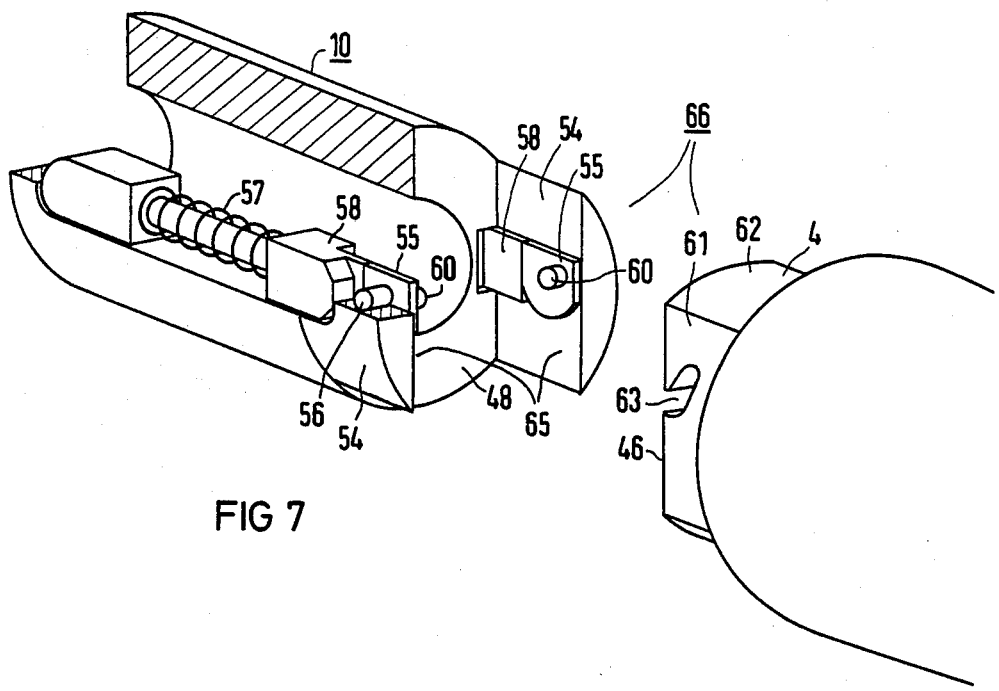
FIG. 7 is a perspective view of parts of the present invention with portions broken away for purposes of illustration of a releasable connection of the present invention.
Figure 8:
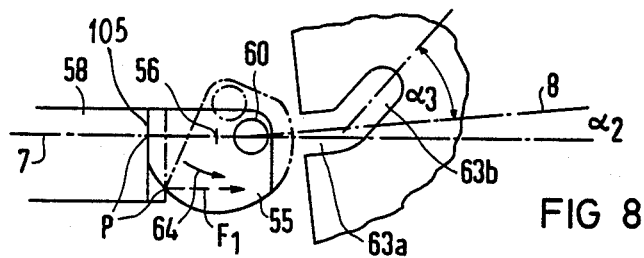
FIG. 8 illustrates the relative position of said parts of the connection of FIG. 7 while disconnected.

A snap-in means 66 for releasably connecting the head part to the handpiece part or grip section is best illustrated in FIGS. 6, 7, 8 and 9. As best illustrated in FIG. 7, the handpiece member 10 adjacent the end surface 48 has a pair of projections or protrusions 54,54 which have flat inner surfaces 65,65. As illustrated in FIG. 7, the surfaces 65,65 are substantially parallel and however they can also be non-parallel as illustrated by surface 65a in FIG. 6. A plate or disc 55 is mounted for rotation on each of the surfaces 65,65a by an axel or pin 56 (FIG. 7). Each of the plates has a curved periphery extending into a flat surface 105 (FIG. 8). This member 10 has a thrust pin 58, which is mounted to move along a path extending parallel to the axis of the body 10 and is urged by a spring 57 into engagement with the flat surface 105. Each of the disc 55 is also provided with a peg or shaft 60, which is mounted eccentrically or offset a distance d to the axel 56.

Figure 9:
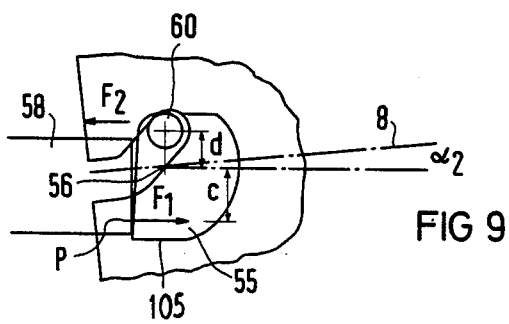
FIG. 9 illustrates the position of the parts of the releasable connection when engaged in forming the connection.

When a connection is made, each peg 60 is received in a slot such as 63 arranged in a side plate 61 of a guide part 62 which is part of the tubular construction of the head part 4. As best illustrated in FIGS. 8 and 9, each of the slots 63 has two portions 63a and 63b. The portion 63a extends parallel to the axis 8 and therefore at an angle $\alpha_2$ to the axis 7. The slot 63b extends at an angle $\alpha_3$ to the axis 8.

When the head part 4 is inserted into the basic body 10, the section 63a of the slot 63 engages the peg 60. Due to the small angle $\alpha_2$, this causes a gradual counterclockwise rotation in a direction of arrow 64 of each of the plates 55 on the axel 56. This counterclockwise rotation is opposed by the force of the spring 57 acting on the pin 58 until the flat surface 105 moves to a position where the spring 57 of the pin 58 has been compressed to the maximum amount of the force. With continued counterclockwise rotation of the plate 55, the spring 57 expands so that its force begins to aid in rotating the plate on axel 56. At this point, the plate has reached a dead center position and further rotation of the plate is thus assisted by the pin 58 and spring 57. When the peg 60 reaches the position such as illustrated in FIG. 9, a force $F_1$ which is exerted by the compression pin 58 at a distance c from the axel will then equal a force $F_2$ acting on the peg or pin 60 at a distance d from the axis of the axel according to the equation $F_1 \cdot c = F_2 \cdot d$. The force $F_1$ is exerted by the spring 57 and the interval of the force p increases with the further amount of rotation in the direction 64.

After passing the dead center position, the head part 4 will be automatically drawn into the connection due to the force of the thrust pin such as 58. To unlock the two handpiece parts, the head part 4 need only be pulled off in axial direction. Initially during disconnection, the peg 60 will be initially guided in the slot 63b to turn the disc 55 around the axel 56 until finally an unlock position such as illustrated in FIG. 8 will be obtained. The force p of the thrust pins 58 will oppose the unlocking until such time as the plate 55 has past over the dead center position relative to the thrust pin 58. In should be noted, that the disc or plate 55 can be shaped in such a manner that instead of a sudden surge of pressure to join the two members occurring after the disc or plate has rotated beyond the dead center position, the increase of the force for joining the members together is gradual due to the curvature of the member.

It should be noted that whether or not the surface of the side portion 61 and the surfaces 65 are parallel to each other or are in a V-shaped configuration as illustrated by surface 65a in FIG. 6, a socket connection between these meeting surfaces prevents twisting between the member 10 and head part 4. In other words, the surface 65,65 and surface 48 form a socket to receive the portion 62 of the part 4.

In the embodiment just described, the insertion of the head part 4 automatically causes movement of the second shaft section 14 to the desired first or second position depending on the length of the interval between the surface 47 and the surface 46. It is also possible to design the structure so that the displaceable drive shaft sections is mechanically displaced by means of an actuation element and in which the neighboring drive shaft sections of the head part has concentric gears similar to the concentric gear arrangement illustrated for the shaft 16 in FIG. 2. In this arrangement, the head part need not be removed to change the ratio which would then be accomplished by means of shifting the shaft 14 between one of two positions.

The sleeve member 38 need not be directly connected to the head part 4. Thus the sleeve 38 may be fixed on the basic body member 10 prior to inserting the head part 4. Because of the conical shape of the part 10 and of the interior shape of the sleeve, a twisting of the part 10 in the sleeve 38 would be prevented. After assembling the sleeve on the member 10, the head part can be inserted.

An embodiment of the handpiece is generally indicated at 100' in FIG. 10 and includes a basic body member 70, which is composed of two sub sections 70a and 70b that are connected together by a friction type locking means such as a snap lock means 71 described hereinabove with regard to FIGS. 6–9. The basic body member 70 is mounted for rotation on an axis of the drive motor housing of the drive motor part 2 by being telescopically received in a sleeve 11. As in the previous embodiment, the member 70 can be maintained by means of stop-bolt 13 received in an annular groove. As mentioned hereinabove, the two sections 70a and 70b are connected together by a snap-lock means generally at 71 with the body section or portion 70a expediently containing the parts of the mechanism 66 of FIG. 7 that were contained by the part 10 and the basic body section or part 70b containing parts of the snap-in means that were contained by the part 4. In the connected state the front faces of the section 70a and 70b corespond with one another and lie rigidly against one another.

A first drive shaft section 72 is rotatably mounted in the basic body section 70a and is coupled with the drive shaft 26 of the drive motor by a coupling 30. Drive shaft 72 contains a conical first gear 73 and a second conical gear 74 which is axially spaced a distance or an interval f from the gear 73. The gear 74 has its teeth extending towards the axis of the shaft 72. Means 102' mounts a second shaft section 78 for axial movement between two positions in a bore or passageway 101'. As illustrated, the shaft 78 on one end has a spur gear 75 and on the other end extends into a housing 76 of the head part 77 and has a conical gear 79 which meshes with a conical gear 81 of a drive shaft section 82 whose axis 88 is at right angles to an axis 80 of the shaft 78. The drive shaft section 82 includes an acceptance socket for the tool which is mounted in the head part 77. A sleeve 83 which covers a significant part of the length of the basic body 70 is rigidly connected to the head part 77.

The means 102' includes a tubular sleeve or guide bushing 84, which rotatably mounts the drive section 78 which may be subdivided into sections 78a and 78b which are interconnected by a coupling 97. The sleeve is slideably received in the bore 101' and has a shoulder engaged by a spring acting on a stop ring to bias the sleeve and the shaft in a direction of arrow 110. In the position illustrated in FIG. 10, the gear is in engagement with the gear 73. The gears 73 and 75 may be designed to have the same number of teeth and therefore provide a 1:1 direct ratio or as illustrated provided a slightly step-down in the RPM for example a ratio of 1.2:1. In order to achieve a standard step-down of the RPM in the device illustrated in FIG. 10 from the drive motor 2 to the tool and a total ratio of 2.7:1, additional step-down ratio of 2.2:1 is undertaken between the gears 79 and 81 in the head housing 76. When the shaft section 78 is shifted to the other position, as illustrated in FIG. 11, the gear 75 is then in engagement with the gear 74 to provide a step-up ratio of approximately 1:3. This can either be accomplished by a complete step-up ratio being accomplished between the gears 74 and 75 or the ratio can be obtained in two steps with a partial amount of the 1:3 step-up ratio being obtained at the gears 74 and 75 and a second part being accomplished in the head section 76a between the gears 85 and 86. As illustrated in FIG. 11, a shaft section 78c is supported in the head section having a gear 85 meshing with the gear 86 on the socket which is rotatably mounted in the housing 76a of the head part 77a.

The exact meshing in FIGS. 10 and 11 is achieved by a detent surface 87 on the sleeve-like portion of the housing 76 acting through a sleeve 108 to act on the sleeve member 84. In FIG. 11, the detent surface 87a acts on a sleeve 108a. Since the sleeves 108a and 108 are the same length, the distance of the sleeve detent surface 87 from the axis 88 from the axis has an interval g and will shift the shaft 78 to a first position with the gear 75 being meshed with the first gear 73. With the interval between the surface 87a and the axis 88a being a distance or interval h, the gear 75 will be meshed with the second gear 64. In the embodiment 100' of FIGS. 10 and 11, the shifting of the gears are again accomplished by inserting of the head part such as 77 or 77a onto the handpiece.

In the embodiment 100' of the handpiece, the head part 77 or 77a along with the sleeve 83 which is rigidly secured thereto are attached to the basic members 70b by means of operationably releasably snap-in mechanism 89. As illustrated, the snap-in mechanism or means 89 consists of a leaf spring 90 fastened to the basic body section 70b. This leaf spring 90 is provided with a stop bold 91 which is engaged in a corresponding groove 92 in the sleeve 83 and thus connects the sleeve together with the head part to the basic body 70b against axial slippage. The mechanism can be unlocked by means of radial actuation of a press button 93, which urges the stop bolt 91 out of the groove 92. After depressing the button 93, the sleeve 83 and the head part 77 can be pulled off of the basic body 70 and subject to a desired sterilization while the drive shaft 78 remains on the basic body.

If one wishes to have a straight handpiece embodiment then either the basic body member 70b is removed from section 70a, which can be achieved by means of an axial pulling of the two parts 70a and 70b apart as described with regard to the snap-in means 66 in FIGS. 6–9 or if the head part with the sleeve 83 is still situated on the basic body 70, then the drive motor part 2 and the sleeve 83 can be axially pulled apart without actuation of the button 93 to disconnect the portion 70b from the portion 70a. A straight ahead part 94 (FIG. 12) with the drive shaft section 95 can now be coupled by the snap-in means onto the basic body portion 70a. Drive shaft 95 has a centrally arranged conical gear 73 with inwardly extending teeth which gear will engage the gear 73 in a direct drive relationship.

Figure 5:
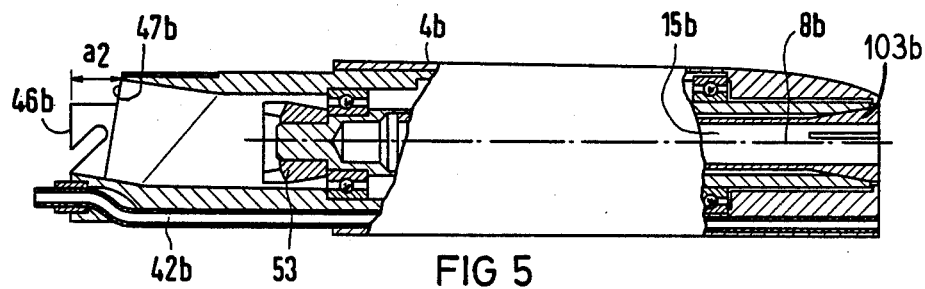
FIG. 5 is a partial longitudinal cross section of a straight head part utilized with the handpiece of the present invention.

In order to put a straight head part similar to the design of FIG. 5 onto the handpiece 100' in place of the angled head part 77, a displaceable drive shaft portion 78 is provided with a coupling 97 which enables subdividing a drive shaft section into two drive sections 78a and 78b. The guide bushing has also been subdivided into two portions 84 and 108.

In order to guarantee a jam free changeover from one gear position to the other gear position, the gears 73 and 74 as well as the gears 25 and 27 of the drive shaft sections 17 and 16, respectively, are laid out in such a manner that the ratio of their number of teeth amounts to a whole multiple, for example 10:30.

Significant advantages of the two described embodiments are that the drive shaft parts which are allocated to the respective handpieces up to now and the corresponding seating parts for seating these drive shaft sections, are now arranged on a drive side part of the handpiece arrangement. Thus, in order to obtain a step-down as well as a step-up of the RPM from the drive motore to the tool, only one handpiece part such as the basic body member 10 or 70 is required and this member receives the head parts, which are significantly simpler to design with the sleeve releasably arranged thereon as shown in FIG. 2 or permeably arranged thereon as shown in FIG. 10.

A further significant advantage is that the rotary connection, which enables transfer of the cooling medium from the drive motor portion or part 2 to the rotatable handpiece part or grip section 3 need not be separated when attaching or disconnecting the head part 4. Accordingly, the O-ring seals of the rotatable connections between the drive motor part and the grip section are subjected to a reduced amount of wear.

Another advantage, particularly, in the embodiment 100′ is that after removal of the head part, a majority of the drive shaft sections and their bearing such as the section 78b of FIG. 10 remain with the drive motor part 2 and therefore are not subjected to any sterilization, which is applied to the head part and the sleeve such as 83. In addition, the embodiment of FIG. 10 has the advantage that a portion of the basic body member 70b can be removed from the basic body section 70a, which is secured on the motor housing so that a straight head part with an appropriately designed drive shaft section as illustrated in FIG. 12 can be connected to the basic body section 70a. The basic body section 70a with the rotatable connection for the media transfer does not need to be separated from the drive motor part in order to form a straight handpiece embodiment.

Although various minor modifications may be suggested by those versed in the art, it should be understood that we wish to embody within the scope of the patent granted hereon, all such modifications as reasonably and properly come within the scope of our contribution to the art.

We claim:

1. In a dental handpiece having a drive motor, an acceptance socket for a tool being mounted for rotation in the head part of the handpiece, and a drive means for transmitting the rotary motion of said drive motor to said acceptance socket, said drive train means including at least two drive shaft sections with the axis of a pair of said sections being arranged at an angle to one another, the first drive shaft section of the pair having a first and second coaxial drive gears with each gear having a different number of teeth, the second drive shaft section of said pair having at least one gear, and means for selectively forming a first coupling and a second coupling between the first and second shaft sections, said first coupling having the first gear of the first shaft section being in engagement with a gear on the second shaft section and the second gear being out of engagement and the second coupling being formed by the second gear of the first shaft section being in engagement with a gear on the second shaft and the first gear being out of engagement, said first coupling having a different drive ratio between the first and second shafts than the drive ratio for the second coupling, the improvements comprising said means for selectively forming the first and second couplings including means for mounting one of said first and second shaft sections for axial movement between a first position forming the first coupling and the second position forming the second coupling, and means for axially displacing said one shaft section between said first and second position, said one shaft section being arranged between a drive shaft section coupled to the drive motor and the head part of the handpiece and having at least one gear at each of the two ends, each of said gears at each end of the one shaft section being in engagement with a gear during at least one of said first and second coupling positions.

2. In a dental handpiece according to claim 1, wherein the first and second gears are disposed in axial spacing on the first shaft section, said spacing having a given axial interval, and said means for moving the one shaft section between said first and second position moving said second shaft section so that a said first and second couplings can be made.

3. In a dental handpiece according to claim 2, wherein said second shaft section being provided with a first and second gear axially spaced thereon by a second interval less than the first mentioned interval, the second gear of the one of said first and second shaft sections and has teeth extending inwardly towards the axis of said shaft section, said means for displacing having said one shaft by a distance equal to a difference between said first and second intervals so that in the first coupling position the first gears of the two shaft sections are engaged to form a first coupling and in the second position, the second gears of the shaft sections are engaged to form the second coupling.

4. In a dental handpiece according to claim 3, wherein the first gears are selected to provide a direct transmission with a drive ratio of 1:1 therebetween, and the second gears being selected so that a step up of the RPM of the second shaft section to the first shaft section is obtained in a ratio range of 1:2.4 through 1:2.6.

5. In a dental handpiece according to claim 3, wherein the first gears have the same number of teeth to provide a direct drive with a ratio of 1:1 and the second gears have a number of teeth selected so that a step down ratio decreased the number of RPM's in the second shaft section, said step down ratio being arranged in a range of 2.4:1 through 2.6:1.

6. In a dental handpiece according to claim 1, wherein the coaxial gears on the first drive shaft are coaxially conical gears with the first gears having exterior disposed teeth and the second gear being concentrically arranged relative to the first gear and having conical teeth extending axially inward.

7. In a dental handpiece arrangement according to claim 6, wherein the means for mounting said one shaft section mounts the section in a handpiece part having a rotatable connection to the housing for the drive shaft so that the housing part can rotate on the axis of the motor housing, said head part being provided with a sleeve member extending over said handpiece part and said handpiece including snap-in means for releasably connecting the head part to said handpiece part.

8. In a dental handpiece according to claim 7, wherein said handpiece part is formed by a first and second member, said first member being relatively short and having bearings supporting said first shaft section for rotation, said second member being longer than said first member and supporting said means for mounting the one drive shaft, and snap-in means for releasable connecting the first and second members together in a frictional type locking arrangement, said snap-in means including means preventing relative twisting between said members.

9. In a dental handpiece arrangement according to claim 8, wherein said one drive shaft section has a length so that one end extends into the head part, said one end having a gear for coacting with a gear disposed on a drive section forming the acceptance socket of the head part.

10. In a dental handpiece according to claim 9, wherein said one drive shaft section is composed of a pair of members axially connected together by means of a releasable coupling.

11. In a dental handpiece according to claim 1, wherein said gear train includes a third drive shaft section, said third drive shaft section being coupled to the second drive shaft section and having its axis extending at an angle to said second drive shaft section, said second drive shaft section being said one drive shaft section mounted by the means for mounting, said first drive shaft section being coupled directly to the drive shaft of the drive motor, and said third drive shaft section being coupled directly to the acceptance socket.

12. In a dental handpiece according to claim 11, wherein the first drive shaft is mounted for rotation in said handpiece part, said handpiece part being mounted for rotation on an axis of a housing of the drive motor and said head part being removably mounted on the other end of said handpiece part.

13. In a dental handpiece according to claim 11, wherein the axes of the three shaft sections are inclined towards one another by an angle in a range of approximately 8° to 12°, said first drive section extending parallel to the longitudinal axis of symmetry of the drive motor, and wherein the total angle of inclination in the handpiece is formed in stages by said angles between said shaft sections.

14. In a dental handpiece according to claim 1, wherein the means for axially displacing the one shaft between said two positions is disposed in said handpiece adjacent said one shaft section.

15. In a dental handpiece according to claim 1, wherein the means for mounting said one shaft includes a sleeve member rotatably mounting said one shaft section, said sleeve member being received in a bore of a handpiece part and having one end engaged by a portion of the head part as it is coupled onto the handpiece.

16. In a dental handpiece according to claim 15, wherein the means for mounting includes a spring biasing the sleeve member from one of said first and second positions in the direction of the other of said first and second positions and stop means limiting the amount of displacement from said one position to a distance greater than the axial distance between said first and second positions.

17. In a dental handpiece according to claim 1, wherein said first drive shaft section is mounted for rotation in a tubular bushing, said bushing being releasably secured in a handpiece part and said first drive shaft sections being releasably coupled to the drive shaft of the drive motor by means of a coupling.

18. In a dental handpiece according to claim 1, wherein the means for mounting is disposed in a handpiece part and the head part is releasably connected to said handpiece part, said handpiece including a sleeve member removably secured thereto and telescopically receiving at least a portion of said handpiece part.

19. In a dental handpiece according to claim 18, wherein said means for connecting comprises a snap-in mechanism for releasably connecting the head part to the handpiece part.

20. In a dental handpiece according to claim 1, wherein the means for mounting the one drive section comprises a sleeve member disposed in a bore of a handpiece part, said sleeve member being cartridge-like and enable interchanging said one drive section.

21. In a dental handpiece according to claim 1, wherein the ratio of the number of teeth of the first and second gears is a whole multiple.

22. In a dental handpiece having a drive motor, an acceptance socket for a tool being mounted for rotation in the head part of the handpiece, and a drive means for transmitting the rotary motion of said drive motor to said acceptance socket, said drive train means including at least two drive shaft sections with the axis of a pair of said sections being arranged at an angle to one another, the first drive shaft section of the pair having a first and second coaxial drive gears with each gear having a different number of teeth, the second drive shaft section of said pair having at least one gear, and means for selectively forming a first coupling and a second coupling between the first and second shaft sections, said first coupling having the first gear of the first shaft section being in engagement with a gear on the second shaft section and the second gear being out of engagement and the second coupling being formed by the second gear of the first shaft section being in engagement with a gear on the second shaft and the first gear being out of engagement, said first coupling having a different drive ratio between the first and second shafts than the drive ratio for the second coupling, the improvements comprising said means for selectively forming the first and second couplings including means for mounting the second shaft section for axial movement between a first position forming the first coupling and the second position forming the second coupling, said second drive shaft section being arranged between a drive shaft coupled to the drive motor and the head part of the handpiece, and means for axially displacing said second shaft section between said first and second position, said first and second gears being disposed in axial spacing on the first shaft section, said spacing having a given axial interval, said first gear being a conical gear with its teeth extending toward the exterior, said second gear having a larger number of teeth and being arranged around the first gear with its teeth pointing inwardly towards the axis, said second shaft having a single conical gear for meshing with the first and second gears when the one shaft is moved between the first and second positions.

23. In a dental handpiece having a drive motor, an acceptance socket for a tool being mounted for rotation in the head part of the handpiece, and a drive means for transmitting the rotary motion of said drive motor to said acceptance socket, said drive train means including at least two drive shaft sections with the axis of a pair of said sections being arranged at an angle to one another, the first drive shaft section of the pair having a first and second coaxial drive gears with each gear having a different number of teeth, the second drive shaft section of said pair having at least one gear, and means for selectively forming a first coupling and a second coupling between the first and second shaft sections, said first coupling having the first gear of the first shaft section being in engagement with a gear on the second shaft section and the second gear being out of engagement and the second coupling being formed by the second gear of the first shaft section being in engagement with a gear on the second shaft and the first gear being out of engagement, said first coupling having a different drive ratio between the first and second shafts than the drive ratio for the second coupling, the improvements comprising said head part being detachable connected to the handpiece, said means for selectively forming the first and second couplings including means for mounting one of said first and second shaft sections for axial movement between a first position forming the first coupling and the second position forming the second coupling, and means for axially displacing said one shaft section between said first and second position, said means for axially displacing the one shaft section including a portion of said head part engaging the means for mounting as the head part is detachable connected to the headpiece.

24. In a dental handpiece having a drive motor, an acceptance socket for a tool being mounted for rotation in the head part of the handpiece, and a drive means for transmitting the rotary motion of said drive motor to said acceptance socket, said drive train means including at least two drive shaft sections with the axis of a pair of said sections being arranged at an angle to one another, the first drive shaft section of the pair having a first and second coaxial drive gears with each gear having a different number of teeth, the second drive shaft section of said pair having at least one gear, and means for selectively forming a first coupling and a second coupling between the first and second shaft sections, said first coupling having the first gear of the first shaft section being in engagement with a gear on the second shaft section and the second gear being out of engagement and the second coupling being formed by the second gear of the first shaft section being in engagement with a gear on the second shaft and the first gear being out of engagement, said first coupling having a different drive ratio between the first and second shafts than the drive ratio for the second coupling, the improvements comprising said means for selectively forming the first and second couplings including means for mounting one of said first and second shaft sections for axial movement between a first position forming the first coupling and the second position forming the second coupling, said one shaft section comprising a tubular member mounted for rotation in a sleeve member forming part of the means for mounting said one shaft section, said tubular member supporting a shaft at each end with each shaft having a pair of axially spaced gears disposed thereon, and means for axially displacing said one shaft section between said first and second position.

25. In a dental handpiece having a drive motor, an acceptance socket for a tool being mounted for rotation in the head part of the handpiece, and a drive means for transmitting the rotary motion of said drive motor to said acceptance socket, said drive train means including at least two drive shaft sections with the axis of a pair of said sections being arranged at an angle to one another, the first drive shaft section of the pair having a first and section coaxial drive gears with each gear having a different number of teeth, the second drive shaft section of said pair having at least one gear, and means for selectively forming a first coupling and a second coupling between the first and second shaft sections, said first coupling having the first gear of the first shaft section being in engagement with a gear on the second shaft section and the second gear being out of engagement and the second coupling being formed by the second gear on the first shaft section being in engagement with a gear on the second shaft and the first gear being out of engagement, said first coupling having a different drive ratio between the first and second shafts than the drive ratio for the second coupling, the improvement comprising said means for selectively forming the first and second couplings including means for mounting one of said first and second shaft sections for axial movement between a first position forming the first coupling and the second position forming the second coupling, said means for mounting being disposed in a handpiece part, means for axially displacing said one shaft section between said first and second position, snap-in means for relesably connecting the head part to the handpiece part, said snap-in means including at least one disc shape member mounted on one of said parts for rotation on an axis, said disc having a peg eccentrically mounted relative to said axis and spring means engaging a flat edge of said disc member, the other of said parts having a slot for receiving the peg as the parts are assembled together, so that during connecting the peg is disposed in said slot and the disc member is rotated against the force of the spring means until the further rotation causes the spring means to urge continued rotation in that direction, and a sleeve member being removably secured to said head part and telescopically receiving at least a portion of said handpiece part.

26. In a dental handpiece according to claim 25, wherein the slot has a first portion for engaging the peg extending parallel to the axis of a drive section in the head part and a second portion extending in an acute angle to the axis of the head part so that during insertion of the peg in the slot the amount of rotation is gradual until the peg reaches the second part of the slot.

* * * * *